United States Patent
Chen et al.

(10) Patent No.: US 11,806,184 B2
(45) Date of Patent: *Nov. 7, 2023

(54) METHOD FOR GATING IN TOMOGRAPHIC IMAGING SYSTEM

(71) Applicant: Delta Electronics, Inc., Taoyuan (TW)

(72) Inventors: Sih-Yu Chen, Taoyuan (TW); Jhih-Shian Lee, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/228,219

(22) Filed: Apr. 12, 2021

(65) Prior Publication Data
US 2021/0315534 A1 Oct. 14, 2021

Related U.S. Application Data

(60) Provisional application No. 63/009,168, filed on Apr. 13, 2020.

(30) Foreign Application Priority Data

Apr. 7, 2021 (CN) .......................... 202110372485.7

(51) Int. Cl.
*A61B 6/00* (2006.01)
*A61B 6/03* (2006.01)
*A61B 6/08* (2006.01)

(52) U.S. Cl.
CPC ............ *A61B 6/5223* (2013.01); *A61B 6/032* (2013.01); *A61B 6/08* (2013.01)

(58) Field of Classification Search
CPC ......... A61B 6/032; A61B 6/541; A61B 6/503; A61B 6/037; A61B 6/5217; A61B 6/5288
See application file for complete search history.

(56) References Cited

U.S. PATENT DOCUMENTS 7,477,771 B2 1/2009 Iatrou et al.
10,937,209 B2 3/2021 Lee et al.
(Continued)

FOREIGN PATENT DOCUMENTS

CN 101926676 A 12/2010
CN 104382613 A 3/2015
(Continued)

OTHER PUBLICATIONS

S.M. Johnston et al., Phase-selective image reconstruction of the lungs in small animals using Micro-CT, Physics of Medical Imaging, Proc. of SPIE vol. 7622, 2010.
(Continued)

*Primary Examiner* — Courtney D Thomas
(74) *Attorney, Agent, or Firm* — KIRTON McCONKIE; Evan R. Witt

(57) ABSTRACT

A method for gating in tomographic imaging system includes steps of: (a) performing a tomographic imaging on an object for acquiring a plurality of projection images at different projection angles, wherein a target of the object moves periodically; (b) obtaining a projected position of the target on each of the projection images, wherein the projected position is a center of a target zone on each of the projection images; (c) calculating a parameter value of pixel values in the target zone on each of the projection images, and obtaining a curve of a moving cycle of the target according to the parameter values of the projection images; and (d) selecting the projection images under the same state in the moving cycle for image reconstruction according to the curve of the moving cycle of the target.

10 Claims, 9 Drawing Sheets

(56) References Cited

U.S. PATENT DOCUMENTS

| | | |
|---|---|---|
| 2004/0258286 A1 | 12/2004 | Salla et al. |
| 2006/0120586 A1* | 6/2006 | Iatrou .................... G16H 50/30 382/131 |
| 2008/0253636 A1 | 10/2008 | Deller |
| 2017/0055920 A1 | 3/2017 | Mestha et al. |
| 2017/0156690 A1 | 6/2017 | Yi et al. |
| 2018/0182135 A1 | 6/2018 | Lee et al. |
| 2018/0303377 A1 | 10/2018 | West et al. |
| 2021/0319599 A1* | 10/2021 | Chen .................... G06T 7/0012 |

FOREIGN PATENT DOCUMENTS

| | | |
|---|---|---|
| CN | 103608845 B | 10/2016 |
| CN | 108324303 A | 7/2018 |
| CN | 108634974 A | 10/2018 |
| CN | 105069785 B | 11/2018 |
| CN | 110197713 A | 9/2019 |
| CN | 110312475 A | 10/2019 |
| CN | 110547822 A | 12/2019 |
| DE | 102007053390 A1 | 12/2008 |
| TW | 201444534 A | 12/2014 |
| TW | I514328 B | 12/2015 |
| WO | 2008156764 A1 | 12/2008 |
| WO | 2010025946 A1 | 3/2010 |
| WO | 2015126189 A1 | 8/2015 |

OTHER PUBLICATIONS

Seonyeong Park et al., A Novel Method of Cone Beam CT Projection Binning based on Image Registration, IEEE Trans Med Imaging, Aug. 2017, pp. 1733-7145.

Haraold Seigarth, Md et al., Electrocardiogram-Independent Image Reconstruction in Cardiac Multidetector Computed Tomography Using Retrospective Motion Synchronization, Investigative Radiology, vol. 41, No. 12, Dec. 2006, pp. 898-903.

Geoffrey D. Hugo et al., Advances in 4D radiation therapy for managing respiration: Part I—4D imaging, Z. Med. Phys., 2012, pp. 258-271.

Rachael Martin et al., Evaluation of intrinsic respiratory signal determination methods for 4D CBCT adapted for mice, American Association of Physicists in Medicine, 2015.

Xuan Liu, et al., "A comparison study: image-based vs signal-based retrospective gating on micro-CT", Conference: Developments in X-Ray Tomography XI, Sep. 2017.

J Kuntz, et al., "Fully automated intrinsic respiratory and cardiac gating for small animal CT", Phys. Med. Biol. 55 (2010) 2069-2085.

Soenke H. Battling, et al., "Intrinsic respiratory gating in small-animal CT", Eur Radiol (2008) 18: 1375-1384.

* cited by examiner

METHOD FOR GATING IN TOMOGRAPHIC IMAGING SYSTEM

CROSS-REFERENCE TO RELATED APPLICATION

This application claims the benefit of U.S. Provisional Application No. 63/009,168 filed on Apr. 13, 2020, entitled "Method for Image-based Gating in Tomographic Imaging System", and claims the priority to China Patent Application No. 202110372485.7, filed on Apr. 7, 2021. The entire contents of the above-mentioned patent application are incorporated herein by reference for all purposes.

FIELD OF THE INVENTION

The present disclosure relates to a method for gating in tomographic imaging system, and more particularly to a method for image-based gating in tomographic imaging system.

BACKGROUND OF THE INVENTION

Tomographic imaging system includes computed tomography (CT), positron emission tomography (PET), and single photon emission computed tomography (SPECT), etc. When the tomographic imaging is performed, the light source (e.g. X-ray source) and the detector are regularly moved around the detected object to emit x-ray and acquire image data by 180 (or more) degrees, so as to collect the projection images at different projection angles. Based on the projection images, an image reconstruction is performed by the computer, and the cross-sectional tomographic image of the detected object is formed. Further, the three-dimensional image of the detected object is formed by the multiple tomographic images.

If the detected object is a living body, the organs (e.g. lung, heart) of the detected object may move periodically due to breath or heartbeat. Therefore, the organs of the detected object in the projection images at different projection angles are not static. Accordingly, the formed tomographic image would be blurred due to the movement of the organs.

The gating technique is developed for obviating blurred images caused by the periodical movement of the organs. Conventionally, the gating technique is a prospective gating technique, which is illustrated as follows.

In the prospective gating technique, the tomographic imaging system has to be connected with the external physiological monitoring apparatus, e.g., Electrocardiography (ECG) machine, piezoelectric sensor. The tomographic imaging system synchronizes with the physiological signal to acquire projection images in a specific state of period. An example of prospective gating for tomographic imaging is shown in FIG. 1. It is noted that the projection images are acquired only during the period marked by dashed blocks. Accordingly, the acquired multi-angle projection images under the same physiological period are utilized for image reconstruction. Consequently, the tomographic images under the specific physiological state are obtained, and blurred images caused by movement on the tomographic images can be reduced. However, the disadvantage of this prospective gating technique is that the tomographic imaging system has to be connected with the external physiological monitoring apparatus, which increases the cost a lot. In addition, it is also a technical challenge to synchronize the tomographic imaging system and the physiological monitoring apparatus.

Therefore, there is a need of providing a method for gating in tomographic imaging system to obviate the drawbacks encountered from the prior arts.

SUMMARY OF THE INVENTION

It is an objective of the present disclosure to provide a method for gating in tomographic imaging system. When the tomographic imaging is performed, the projection images with different angles are acquired continuously. After the projection images are all collected, the projection images are processed according to the characteristics thereof. Particularly, the projection images under the same physiological state are selected. Accordingly, in the method for gating in tomographic imaging system of the present disclosure, there is no need to connect the tomographic imaging system with any external physiological monitoring apparatus.

In accordance with an aspect of the present disclosure, there is provided a method for gating in tomographic imaging system. The method includes steps of: (a) performing a tomographic imaging on an object for acquiring a plurality of projection images at different projection angles, wherein a target of the object moves periodically; (b) obtaining a projected position of the target on each of the projection images, wherein the projected position is a center of a target zone on each of the projection images; (c) calculating a parameter value of pixel values in the target zone on each of the projection images, and obtaining a curve of a moving cycle of the target according to the parameter values of the projection images; and (d) selecting the projection images under the same state in the moving cycle for image reconstruction according to the curve of the moving cycle of the target.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
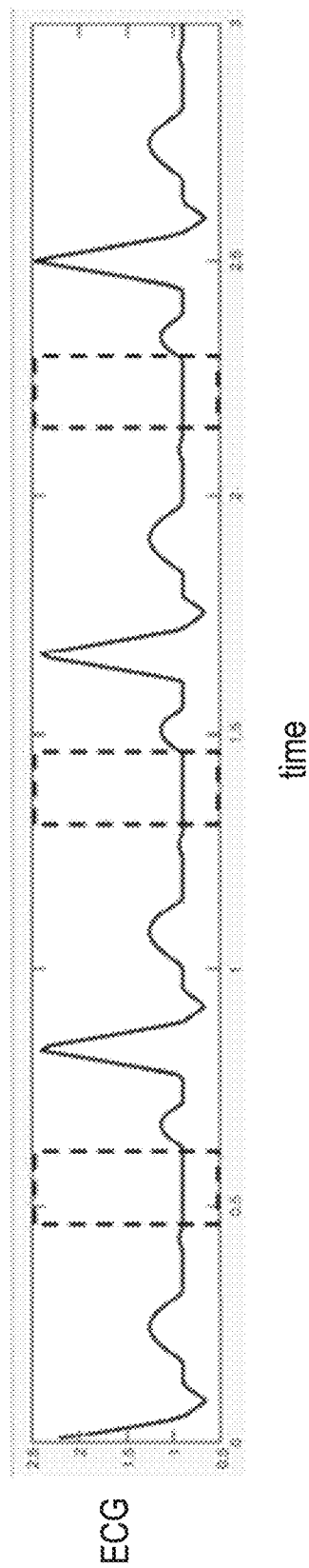
FIG. 1 schematically shows the timing of performing tomographic imaging in the conventional prospective gating method.
Figure 2:
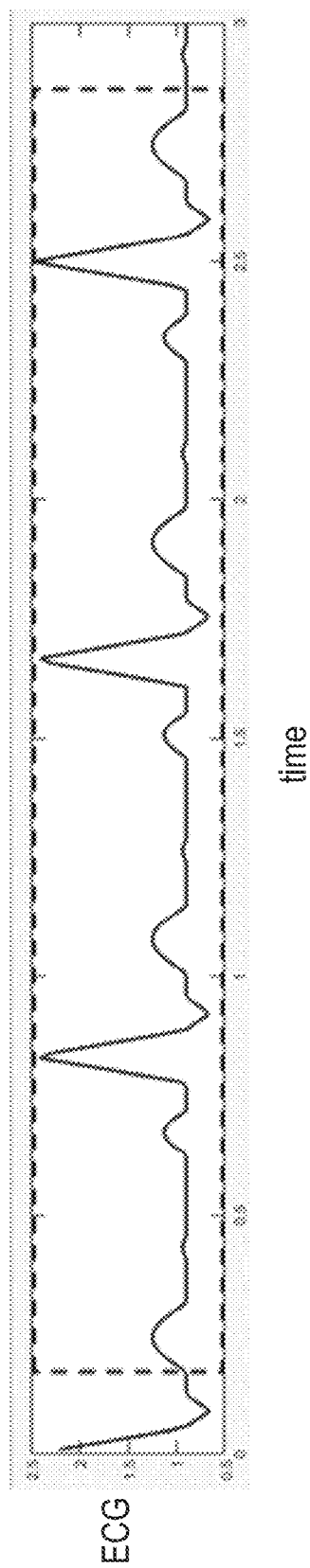
FIG. 2 schematically shows the timing of performing tomographic imaging in a method for gating of the present disclosure.

The method for gating in tomographic imaging system of the present disclosure utilizes a retrospective gating technique. When the tomographic imaging is performed, as shown in FIG. 2, the projection images are acquired continuously during the period marked by dashed block. Particularly, the present disclosure utilizes the retrospective gated tomographic imaging system for gating to obviate blurred images caused by the periodical movement of the organs.

When the tomographic imaging is performed, the light source, e.g., X-ray source, and the detector are regularly rotated relative to a first axis on which the object is located, so as to collect the projection images at different projection angles. The number of the projection images is N, being an integer, which can be determined according to the required image quality of the tomographic image based on the projection images. For example, the larger N is, the better signal to noise ratio of the tomographic image is (i.e., the better image quality of the tomographic image is). In addition, during the light source and the detector moving around the detected object for collecting the projection images at different projection angles, the difference between the first projection angle and the final projection angle is preferably but not limited to be larger than 180 degrees.

If the detected object is a living body, the organs of the detected object may move periodically due to heartbeat. Therefore, the projection images at different projection angles and timings are not static. Accordingly, the tomographic imaging system for cardiac gating is further developed in the present disclosure. In order to figure out the cardiac cycle to which every projection image is corresponding, the position of the organ or zone affected by heartbeat on every projection image should be detected. Taking the heart as an example of a target that moves periodically in the detected object, two embodiments of computing the projected position of the heart on every projection image are described as follows.

Figure 3:
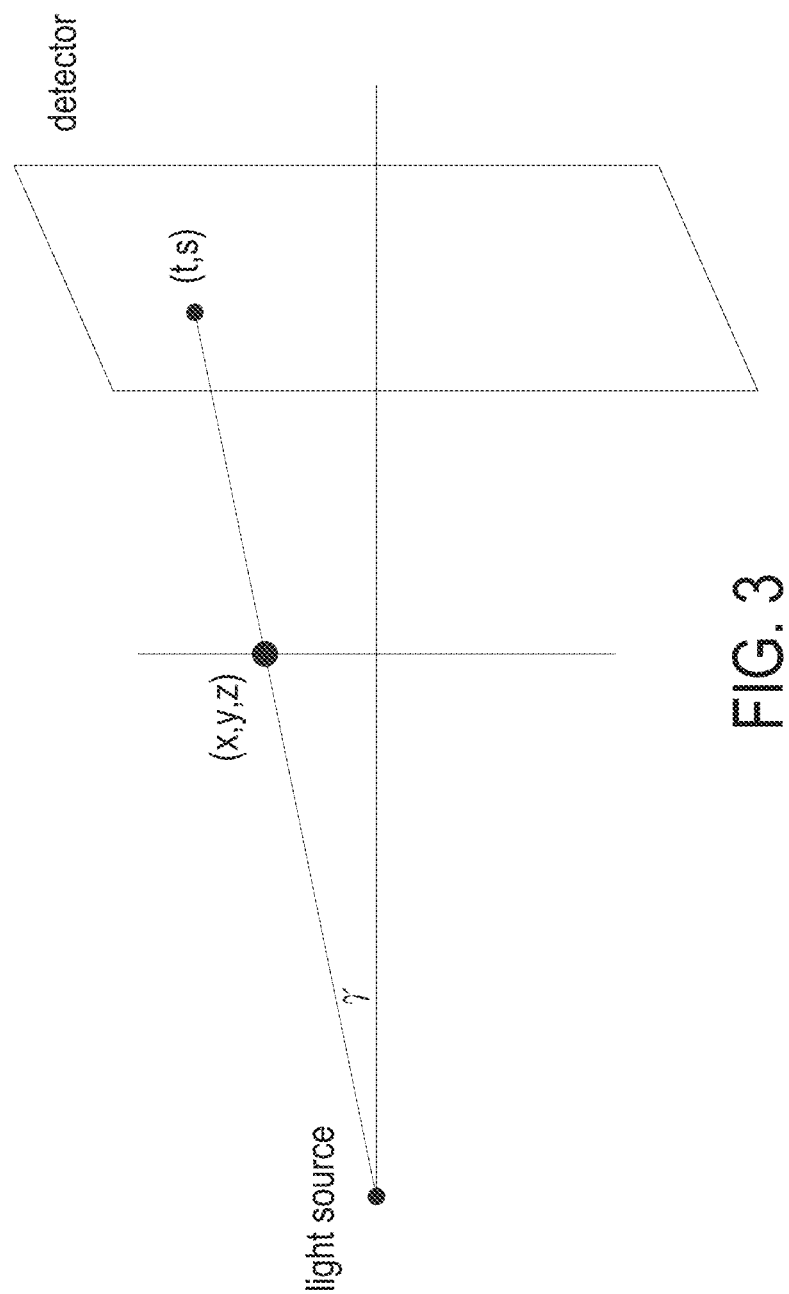
FIG. 3 schematically shows the position relations among the actual position and projected position of the heart, the light source and detector.

Regarding the first embodiment of computing the projected position of the heart in the present invention, the position relations among the actual position of the heart in the three-dimensional space, the projected position of the heart, the light source and the detector are shown in FIG. 3 and equations (1) and (2). In FIG. 3, (x, y, z) is the coordinate of the actual position of the heart in the three-dimensional space, (t, s) is the coordinate of the projected position of the heart on the projection image, θ is the projection angle of acquiring the projection image (i.e., the rotation angle of the light source and the detector), and γ is the cone angle of the light source. The rotation axis of the light source and the detector is the first axis on which the heart is located. There is a second axis perpendicular to the first axis, and the cone angle γ is an included angle between the second axis and a connecting line of the light source and the heart.

$$t = x\cos(\theta) + y\sin(\theta) \quad (1)$$

$$s = -(x\sin(\theta) + y\cos(\theta))\sin(\gamma) + z\cos(\gamma) \quad (2)$$

The projection angle θ and the cone angle γ are known in the tomographic imaging system. Therefore, when the projected positions of the heart on any two projection images are inputted into the tomographic imaging system, the projected position of the heart on the other projection images can be figured out. For example, according to the projected positions of the heart on those two projection images, x and y in the coordinate of the actual position of the heart are calculated through equation (1). When x and y are known, tin the coordinate of the projected position of the heart on every projection image can be obtained by substituting the corresponding projection angle θ into equation (1). Moreover, by substituting the acquired x and y and s, θ and γ corresponding to any projection image into equation (2), z in the coordinate of the actual position of the heart can be figured out. If the height location z of the heart is supposed to be the same, s in the coordinate of the projected position on all the projection images are the same. Consequently, the coordinates of the projected positions of the heart on all the projection images are acquired. In addition, on each projection image, the heart zone is marked automatically by a solid-line block with the projected position as a center, and the heart is projected in the heart zone. The size of the solid-line block may be set by the user based on experience or may be preset by the system.

Figure 4:
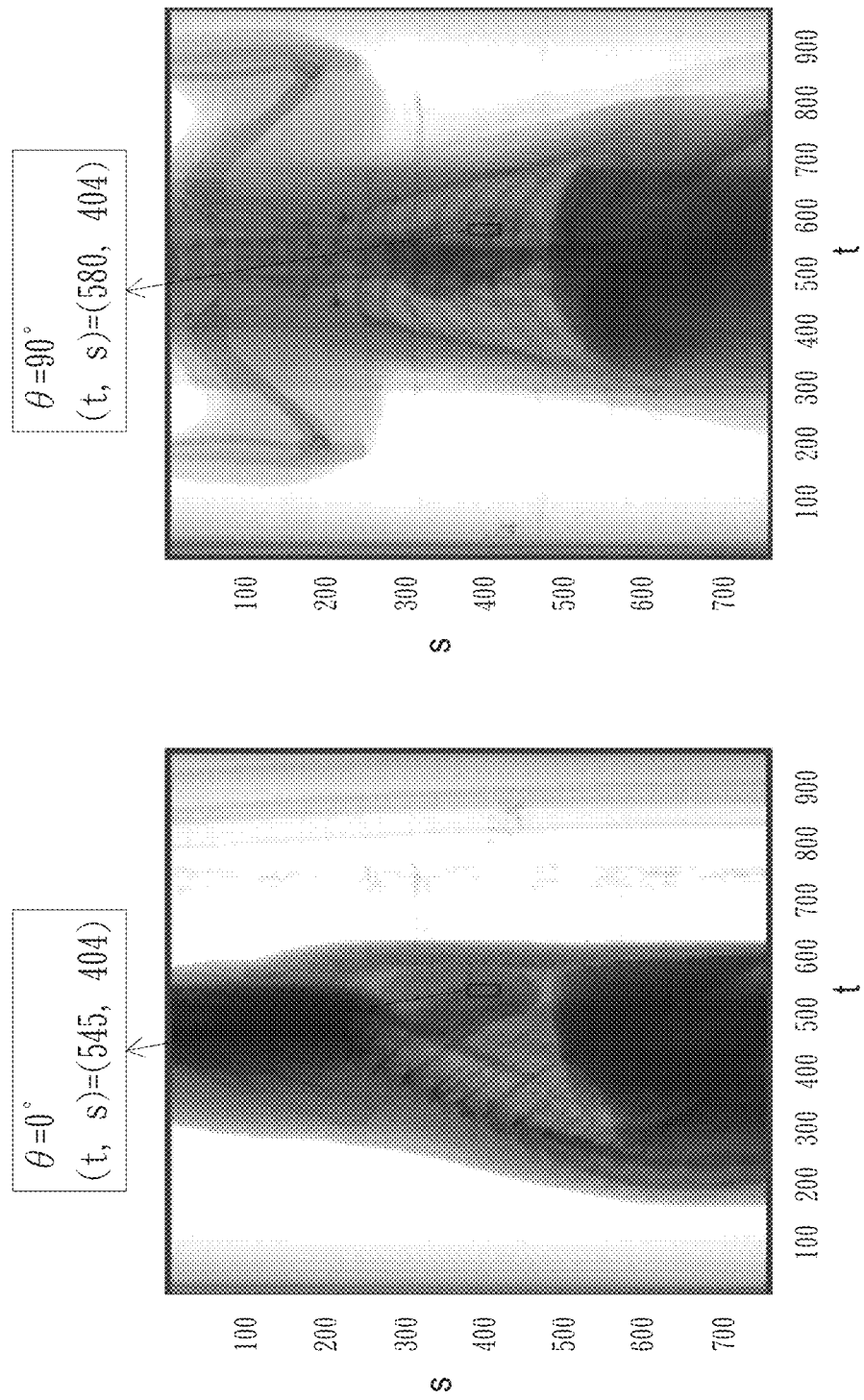
FIG. 4 schematically shows the projection images.

As an example, the tomographic imaging is performed on a mouse, and FIG. 4 schematically shows two projection images, which are acquired at two different projection angles θ, including 0 and 90 degrees, respectively. The user can move the solid-line block for manually defining the projected position of the heart on the two projection images, and the center of the solid-line block is the projected position of the heart. According to the projected positions of the heart on the two projection images, the projected position of the heart on all the other projection images can be calculated through equation (1).

Figure 5:
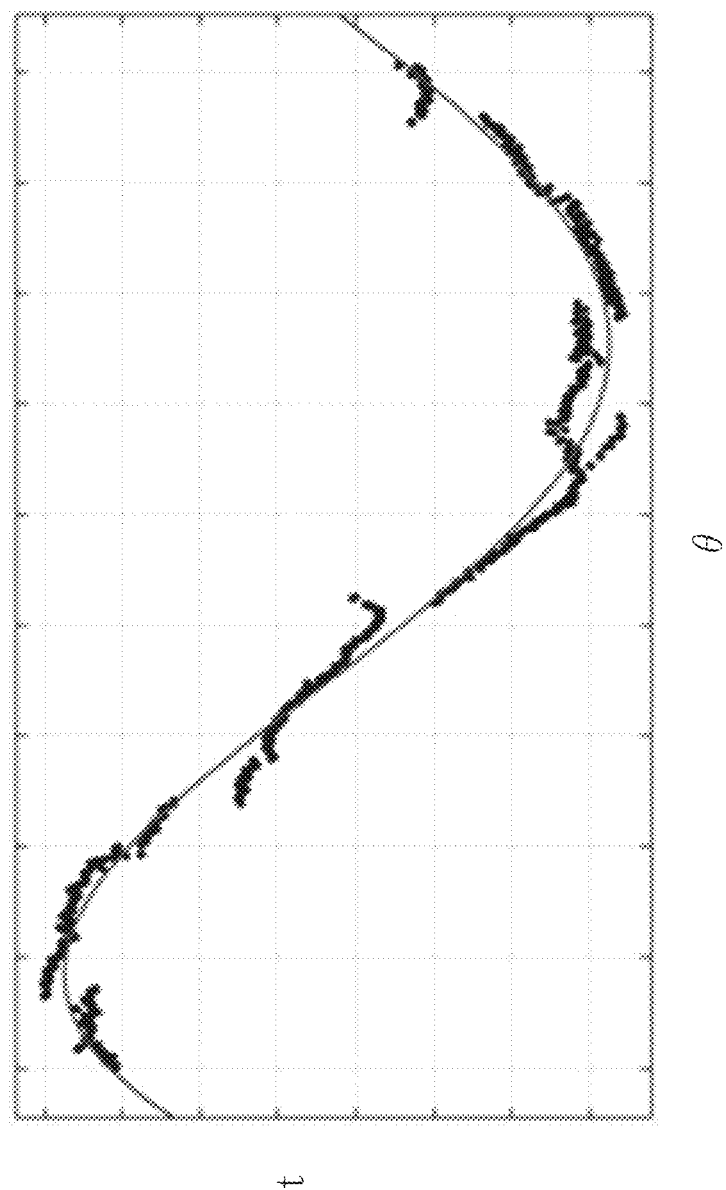
FIG. 5 schematically shows processing the projection angle and the projected position of the heart in every projection image with curve fitting.

Regarding the second embodiment of computing the projected position of the heart in the present invention, firstly, a distance range is set. For example, the distance range is determined according to the size of the heart. Then, the projected position $(t_0, s_0)$ in one projection image $P_0$ is inputted or pointed by the user as a reference point, and the pixel value $I_0$ of the projected position $(t_0, s_0)$ is set as a reference value. Then, on another projection image $P_1$ with unknown projected position, the position $(t_1, s_1)$ having the pixel value $I_1$ closest to the reference value $I_0$ within the distance range from the reference point $(t_0, s_0)$ is set as the projected position of the heart in this projection image $P_1$. Afterwards, the reference point and the reference value are respectively updated by the position $(t_1, s_1)$ and the pixel value $I_1$ for another projection image $P_2$ without unknown projected position. Accordingly, the projected positions of the heart on all the projection images can be figured out. Preferably, the projection image $P_1$ is taken at a different projection angle following the projection image $P_0$, and the projection image $P_2$ is taken at a different projection angle following the projection image $P_1$. The projected position of the heart is the heart in the three-dimensional space projected on the detector during rotation. Then, as shown in FIG. 5, the computed projected positions of the heart on all the projection images can be fitted by sine and cosine curves so as to remove the discontinuous area. Therefore the computed projected positions of the heart on all the projection images can be calibrated. In addition, in each projection image, the heart zone is marked automatically by a solid-line block with the projected position as a center, and the heart is projected in the heart zone. The size of the solid-line block may be set by the user based on experience or may be preset by the system.

Through the two embodiments described above, the projected positions of the heart on all the projection images are acquired, and the heart zone is marked by the solid-line block with the projected position as a center. In another embodiment, the heart zone may be marked by dashed-line block or other marking manner. Then the parameter value (e.g., maximum, minimum, average, median, summation or quartile) of the pixel values in the heart zone on the projection image is calculated. Since the pixel values in the heart zone varies with the heart systole and diastole, the curve of the moving cycle of the heart (i.e., the heartbeat curve) is obtained according to the parameter values of all the projection images. For example, the curve of the moving cycle of the heart is a graph of the parameter value versus time, or a graph of the parameter value versus a serial number of the projection images.

Figure 6:
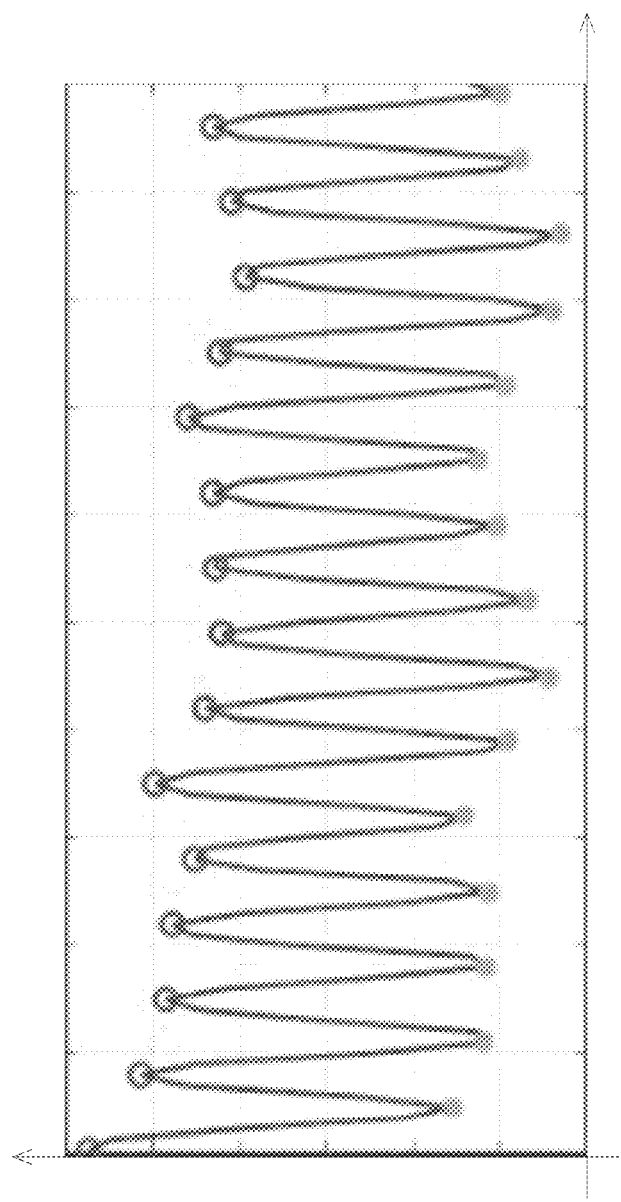
FIG. 6 is a schematic oscillogram showing the heartbeat curve.

As shown in FIG. 6, the heartbeat curve can be obtained according to the parameter values of all the projection images. The projection images under the same state in the cardiac cycle (i.e., the projection images taken at the same timing in the cardiac cycle) are selected for image reconstruction, and the definition of the heart tomographic image is improved. For example, the projection images at the timing marked by the hollow circles are selected for image reconstruction, or the projection images at the timing marked by the solid circles are selected for image reconstruction. In FIG. 6, the transverse axis represents the time or the serial number of the projection images, and the vertical axis represents the parameter value of the pixel values in the heart zone.

Figure 7:
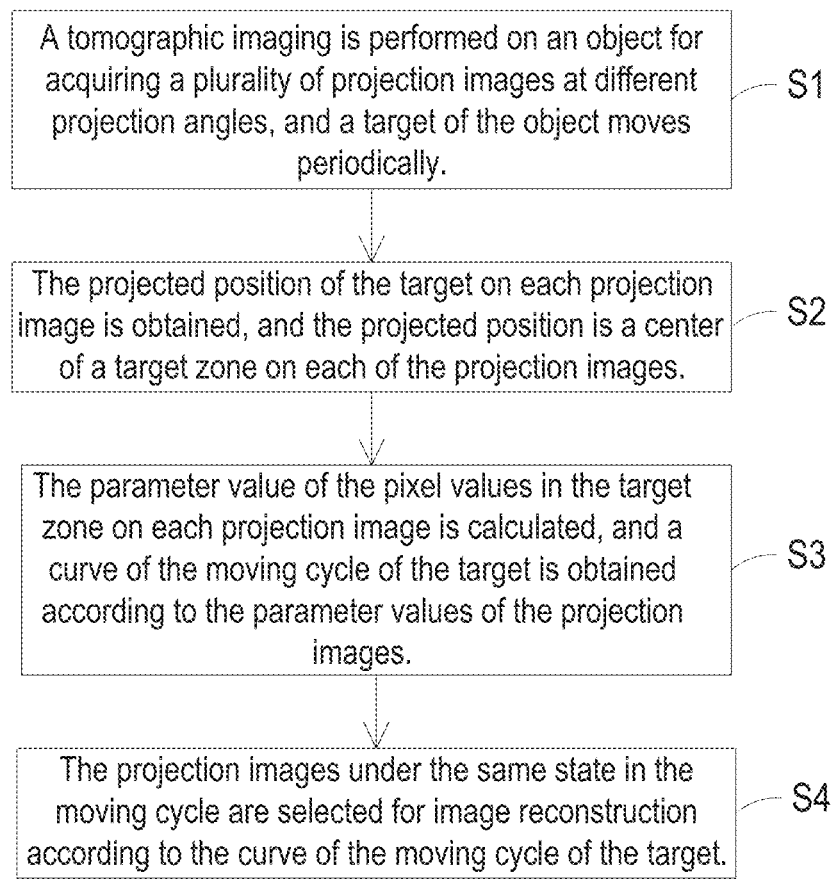
FIG. 7 is a schematic flow chart illustrating a method for gating in tomographic imaging system according to an embodiment of the present disclosure.

FIG. 7 is a schematic flow chart illustrating a method for gating in tomographic imaging system according to an embodiment of the present disclosure. Based on the above illustration, the method for gating in tomographic imaging system of the present disclosure can be generalized to include the steps shown in FIG. 7.

First, in step S1, a tomographic imaging is performed on an object for acquiring a plurality of projection images at different projection angles, and a target of the object moves periodically.

Then, in step S2, the projected position of the target on each projection image is obtained, and the projected position is a center of a target zone on each of the projection images.

Afterward, in step S3, the parameter value of the pixel values in the target zone on each projection image is calculated, and a curve of the moving cycle of the target is obtained according to the parameter values of the projection images.

Finally, in step S4, the projection images under the same state in the moving cycle are selected for image reconstruction according to the curve of the moving cycle of the target.

Consequently, by the method for gating in tomographic imaging system of the present disclosure, the projection images under the same state in the cardiac cycle are picked out for image reconstruction. Meanwhile, there is no need to connect the tomographic imaging system with any external physiological monitoring apparatus.

Figure 8:
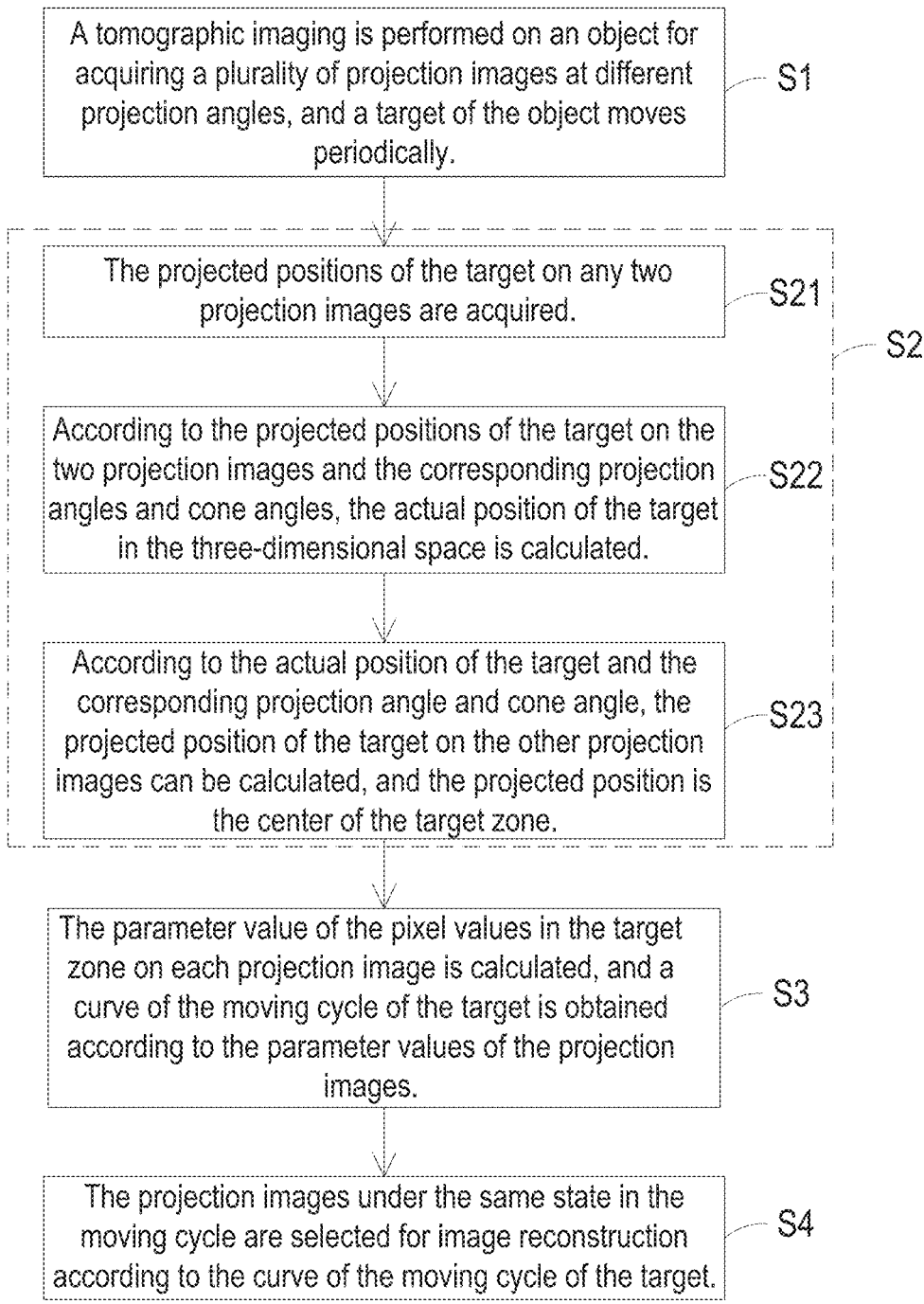
FIG. 8 and FIG. 9 are schematic flow charts showing the variants of the method for gating in tomographic imaging system of FIG. 7.

In an embodiment, as shown in FIG. 8, based on the above-mentioned equations (1) and (2), the step S2 includes the following substeps. Firstly, in substep S21, the projected positions of the target on any two projection images are acquired. Then, in substep S22, according to the projected positions of the target on the two projection images and the corresponding projection angles (i.e., the rotation angles of the light source and the detector) and cone angles, the actual position of the target in the three-dimensional space is calculated. Finally, in substep S23, according to the actual position of the target and the corresponding projection angle and cone angle, the projected position of the target on the other projection images can be calculated, and the projected position is the center of the target zone.

Figure 9:
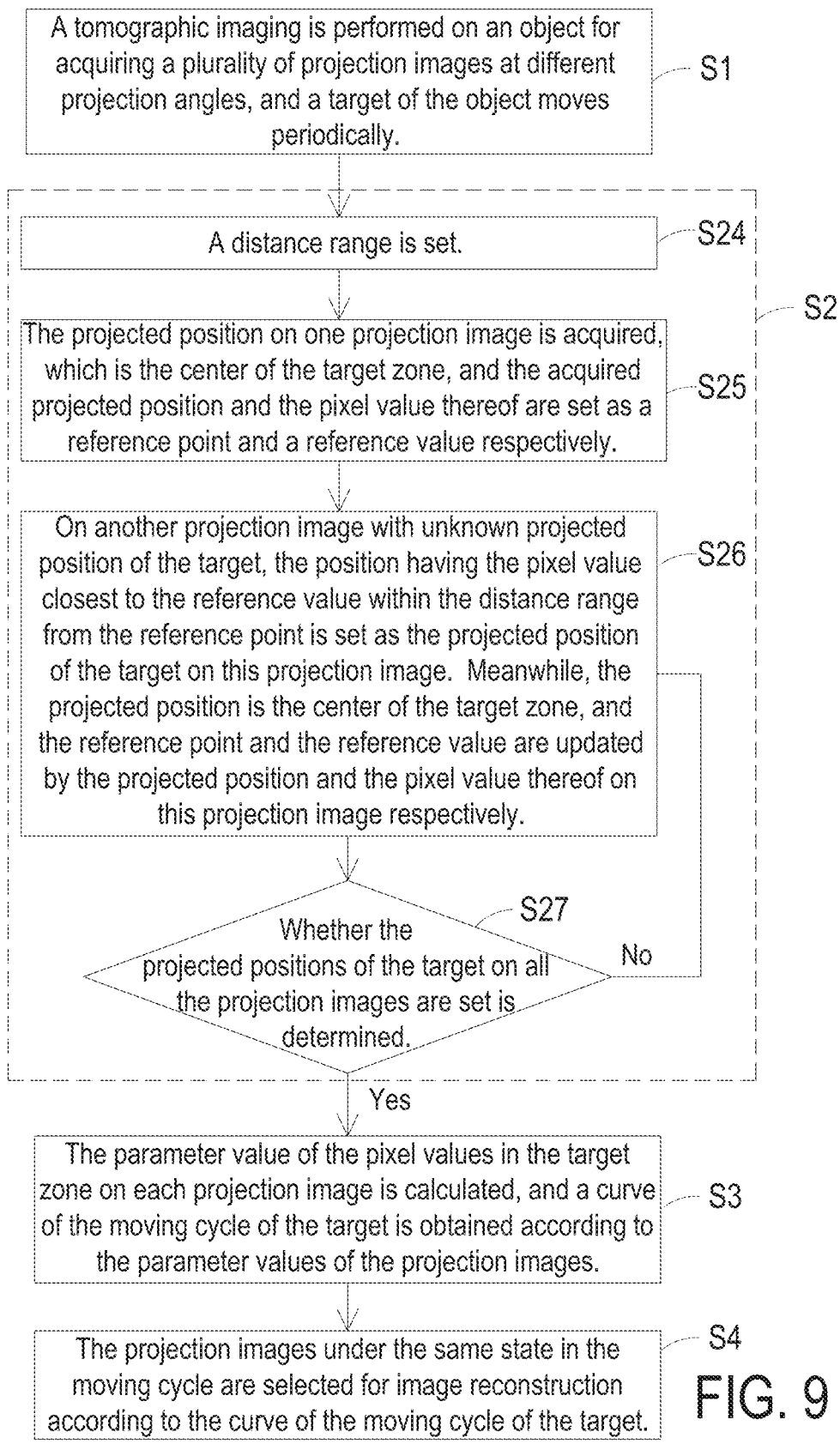

In another embodiment, as shown in FIG. 9, the step S2 includes the following substeps. Firstly, in substep S24, a distance range is set. Then, in substep S25, the projected position on one projection image is acquired, which is the center of the target zone, and the acquired projected position and the pixel value thereof are set as a reference point and a reference value respectively. Afterward, in substep S26, on another projection image with unknown projected position of the target, the position having the pixel value closest to the reference value within the distance range from the reference point is set as the projected position of the target on this projection image. Meanwhile, the projected position is the center of the target zone, and the reference point and the reference value are updated by the projected position and the pixel value thereof on this projection image respectively. Finally, in substep S27, whether the projected positions of the target on all the projection images are set is determined. If the determining result is satisfied, the step S3 is performed. If the determining result is not satisfied, the substep S26 is performed again.

In the embodiment shown in FIG. 9, after the projected positions of the target on all the projection images are acquired, the step S2 further includes a substep of fitting the projected positions on all the projection images by sine and cosine curves, thereby achieving the calibration for the projected positions.

The gating method of the present disclosure may be applied on the embodiments shown in FIGS. 2-6. Further, in the embodiments shown in FIGS. 2-6, the detected object is a living body, and the target is the heart, which moves periodically due to heartbeat. In another embodiment, the target in the gating method of the present disclosure may also be the diaphragm, which moves periodically due to breath.

From the above descriptions, the present disclosure provides a method for gating in tomographic imaging system. When the tomographic imaging is performed, the projection images with different angles are acquired continuously. After the projection images are all collected, the projection images are processed according to the characteristics thereof. Particularly, the projection images under the same physiological state are picked out. Accordingly, in the method for gating in tomographic imaging system of the present disclosure, there is no need to connect the tomographic imaging system with any external physiological monitoring apparatus.

While the disclosure has been described in terms of what is presently considered to be the most practical and preferred embodiments, it is to be understood that the disclosure needs not be limited to the disclosed embodiment.

What is claimed is:

1. A method for gating in tomographic imaging system, comprising:

(a) performing a tomographic imaging on an object for acquiring a plurality of projection images at different projection angles, wherein a target of the object moves periodically;

(b) obtaining a projected position of the target on each of the projection images, wherein the projected position is a center of a target zone on each of the projection images;

(c) calculating a parameter value of all pixel values in the target zone on each of the projection images, and obtaining a curve of a moving cycle of the target according to the parameter values of the projection images; and (d) selecting the projection images under the same state in the moving cycle for image reconstruction according to the curve of the moving cycle of the target.

2. The method according to claim 1, wherein when the tomographic imaging is performed, a light source and a detector are regularly rotated relative to a first axis for acquiring the projection images at the different projection angles.

3. The method according to claim 2, wherein the step (b) comprises substeps of:
(b1) acquiring the projected positions of the target on any two of the plurality of projection images;
(b2) according to the projected positions on the two projection images and the corresponding projection angles and cone angles, calculating an actual position of the target, wherein the first axis is perpendicular to a second axis, and the cone angle is an included angle between the second axis and a connecting line of the light source and the target; and
(b3) according to the actual position and the corresponding projection angle and cone angle, calculating the projected positions on the rest of the projection images.

4. The method according to claim 3, wherein relations among the actual position and the projected position, the projection angle and the cone angle corresponding to each of the projection images satisfy the following equations:

$$t = x\cos(\theta) + y\sin(\theta) \quad (1)$$

$$s = -(x\sin(\theta) + y\cos(\theta))\sin(\gamma) + z\cos(\gamma) \quad (2)$$

where $(x, y, z)$ is a coordinate of the actual position, $(t, s)$ is a coordinate of the projected position, $\theta$ is the projection angle, and $\gamma$ is the cone angle.

5. The method according to claim 1, wherein the step (b) comprises substeps of:
(b4) setting a distance range;
(b5) acquiring the projected position on any of the projection images, and setting the projected position and a pixel value thereof as a reference point and a reference value respectively;
(b6) on another of the projection images with unknown projected positions, setting the projected position of the target having a pixel value closest to the reference value within the distance range from the reference point, and updating the reference point and the reference value by the projected position and the pixel value thereof on the another of the projection images respectively; and
(b7) determining whether the projected positions on all the projection images are set, performing the step (c) if the determining result is satisfied, and performing the substep (b6) if the determining result is not satisfied.

6. The method according to claim 5, wherein after the projected positions on all the projection images are set, the step (b) further comprises a substep of fitting the projected positions on all the projection images by sine and cosine curves.

7. The method according to claim 1, wherein a number of the projection images is determined according to a required image quality of a tomographic image based on the projection images.

8. The method according to claim 1, wherein in the projection angles, a difference between a first projection angle and a final projection angle is larger than 180 degrees.

9. The method according to claim 1, wherein the parameter value is a maximum, a minimum, an average, a median, a summation or a quartile of the pixel values in the target zone.

10. The method according to claim 1, wherein the curve of the moving cycle of the target is a graph of the parameter value versus time, or a graph of the parameter value versus a serial number of the projection images with different projection angles.

* * * * *